United States Patent [19]
Lawson et al.

[11] 3,939,196
[45] Feb. 17, 1976

[54] DIARYLCYCLOBUTANES

[75] Inventors: John E. Lawson; Ronnie D. Dennis; Robert F. Majewski, all of Evansville, Ind.

[73] Assignee: Mead Johnson & Company, Evansville, Ind.

[22] Filed: Feb. 20, 1974

[21] Appl. No.: 444,071

[52] U.S. Cl. ........... 260/613 R; 260/345.9; 260/395; 260/590 C; 260/612 D; 260/618 R; 260/619 B; 424/341; 424/346
[51] Int. Cl.² .................. C07C 39/17; C07C 43/20
[58] Field of Search .................. 260/619 B, 613 R

[56] References Cited
UNITED STATES PATENTS

| 2,864,868 | 12/1958 | Bader | 260/619 B X |
| 3,232,994 | 2/1966 | Apel et al. | 260/619 B |
| 3,357,947 | 12/1967 | Stockmann et al. | 260/619 B X |
| 3,408,407 | 10/1968 | Cotter et al. | 260/619 B |
| 3,437,637 | 4/1969 | Matzner et al. | 260/619 B X |

OTHER PUBLICATIONS

Curtis (I), "Chem. and Ind.," Vol. 1960, p. 928 (1960).
Curtis (II), "J. Chem. Soc.," Vol. 1962, pp. 415–418 (1962).

*Primary Examiner*—Norman Morgenstern
*Attorney, Agent, or Firm*—R. E. Carnahan; R. H. Uloth

[57] ABSTRACT

1,3-bis(p-Hydroxyphenyl)cyclobutane and its monomethyl ether are estrogenic agents having antifertility action.

3 Claims, No Drawings

DIARYLCYCLOBUTANES

FIELD OF THE INVENTION

The compounds of this invention are carbocyclic phenols of the cyclobutane series. They are prepared from starting materials of the styrene series. They are novel compounds and possess biological activity.

DESCRIPTION OF THE PRIOR ART

The compounds of the present invention are substituted diphenylcyclobutane derivatives which possess a formal structural relationship to diethylstilbestrol. The latter is a well-known non-steroidal synthetic estrogen. 3-(p-Methoxyphenyl)cyclobutanone serves as starting material, and is obtained by a process analogous to a process previously reported by Silversmith, et al., J. Amer. Chem. Soc., 80, 5840 (1958) for the preparation of 3-phenylcyclobutanone from styrene.

SUMMARY OF THE INVENTION

This invention provides for the first time compounds of Formulas I and II. The compounds of Formula I in which $R^1$ is hydrogen or methyl are estrogenic agents and have utility as such and as anti-fertility agents. They are prepared from 3-(p-methoxyphenyl)cyclobutanone via the intermediates of Formula II. In Formula II, $R^2$ is methyl, tetrahydropyranyl, benzyl, trityl or tert.-butyl. $R^3$ is hydrogen or hydroxyl. The compounds of Formula II are low potency depressants of the mammalian central nervous system and psychotropic agents for mammals at doses of 250–1000 mg./kg.

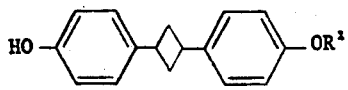

Formula I

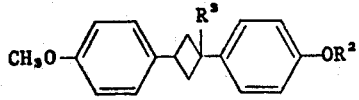

Formula II

DETAILED DESCRIPTION OF THE INVENTION p-Methoxystyrene may be converted to 3-(p-methoxyphenyl)-cyclobutanone according to the method of Silversmith, et al. (loc. cit.) when several modifications of the published procedure are made. These are described below in Procedures 1–4. 3-(p-Methoxyphenyl)cyclobutanone is then converted by the Grignard reaction to the intermediates of Formula II.

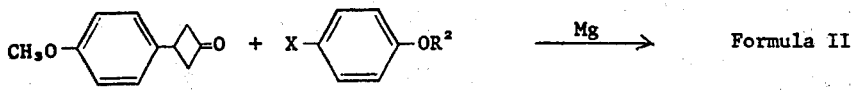

Formula II

In the reaction scheme, the symbol X is in the reactant employed with 3-(p-methoxyphenyl)cyclobutanone represents chlorine, bromine, or iodine and $R^2$ has the same meaning as above. The Grignard reaction shown in the foregoing reaction scheme is carried out under the ordinary conditions known to those skilled in the art for the preparation of Grignard reagents and reaction thereof with ketones. Suffice to say that anhydrous conditions are employed and a liquid, reaction inert, ether such as diethyl ether, tetrahydrofuran, or di-n-butyl ether is employed as reaction medium. The product is recovered after conclusion of the reaction by hydrolysis with water or an aqueous solution of a weak acid such as ammonium chloride.

The intermediates of Formula II are considered part of the present invention and are converted to the products of Formula I by hydrogenolysis of the hydroxyl group when $R^3$ is hydroxyl, and cleavage of the $R^2$ substituent under ordinary conditions for those transformations which are known to those skilled in the art. Convenient hydrogenolysis conditions are disclosed in Procedure 6 and involve the use of a palladium on charcoal catalyst suspended in 95% ethanol containing 1% by volume of 70% perchloric acid as reaction medium and employing an atmosphere of hydrogen at pressures of from about 15 to 50 pounds per square inch.

The $R^2$ substituents of Formula II are groups which are labile to replacement by hydrogen by hydrolysis or hydrogenolysis thereof from the oxygen atom at temperatures of from about room temperature up to temperatures in excess of the melting point of the reactants but below temperatures at which substantial decomposition occurs. A maximum temperature of about 250°C. for cleavage of $R^2$ is employed. When acidic conditions are employed and $R^3$ is OH, dehydration of the cyclobutanol to a cyclobutene derivative occurs. Accordingly, acidic $R^2$ cleavage is either done under hydrogenating conditions, or confined to those instances wherein $R^3$ is hydrogen.

When $R^2$ is the methyl group and $R^3$ is hydrogen, a convenient method involves simply mixing the reactant of Formula II with pyridine hydrochloride and heating the dry mixture at about 210°C. The product is recovered by dilution of the reaction mixture with water and extraction with a water immisible organic solvent. This is illustrated in Procedure 7. The benzyl and trityl groups are readily removed under the aqueous acidic hydrolysis and hydrogenolysis conditions of Procedure 6. Similarly, aqueous acid at room temperature will cleave the tetrahydropyranyl and the tert.-butyl $R^2$ substituents. Again the hydrogenolysis conditions of Procedure 6 are sufficiently acidic to result in cleavage of such $R^2$ substituents.

To summarize, 3-(p-methoxyphenyl)cyclobutanone is reacted with a Grignard reagent prepared from a p-(chloro, bromo or iodo)phenyl $R^2$ ether, hydrolyzing the resulting reaction complex and recovering intermediates of Formula II wherein $R^3$ is hydroxyl. The latter is then converted to the cyclobutane derivative by hydrogenolysis of the $R^3$ OH group and cleavage of the $R^2$ ether substituent.

Estrogenic action is shown for the compounds of Formula I in the uterotrophic assay of Rubin, et al. (Endocrinology, 49, 429 (1950)) employing immature female rats. Doses of 20–80 mg./kg. subcutaneously of 1,3-bis(p-hydroxyphenyl)cyclobutane (Procedure 7) and its monomethyl ether (Procedure 9) daily for 3 days result in statistically significant increases in uterine weight. In the vaginal cornification test in rats (Dorfman's "Methods in Hormone Research", Vol. 2, pages 65–80, Academic Press, 1962) 90% of the ovariectomized animals give a response when challenged with 30 mg./kg. of 1,3-bis(p-hydroxyphenyl)cyclobutane subcutaneously.

The postcoital antifertility action of the compounds of Formula I can be demonstrated in the rat in a test involving daily dosing on the first 6 days of pregnancy and sacrificing on the 8th day. The uterine horns are examined and the total number of normal and abnormal implantation sites for groups of 10 animals are counted. A 50% reduction in normal implantation sites was determined for 1,3-bis(p-hydroxyphenyl)cyclobutane at a dose of 9.7 mg./kg. of body weight subcutaneously. Pregnancy was prevented in all animals of a group of 10 receiving 15 mg./kg. subcutaneously. With 3-(p-hydroxyphenyl)-1-(p-methoxyphenyl)cyclobutane, pregnancy was prevented in all animals in a group of 10 receiving a dose of 40 mg./kg. subcutaneously.

The compounds of Formula I may be employed for estrogenic purposes in much the same way as estrone, but in doses of from about 2 mg./kg. of body weight up to about 500 mg./kg. of body weight orally or parenterally. For antifertility purposes, daily parenteral injection of doses of about 0.1 to 100 mg./kg. of body weight on the first 6 days following coitus is preferred.

The compounds of Formulas I and II have oral lethal toxic doses ($ALD_{50}$) for mice of greater than 1000 mg./kg.

DESCRIPTION OF SPECIFIC EMBODIMENTS

Procedure 1.
2,2-Dichloro-1,1-difluoro-3-(p-methoxyphenyl)-cyclobutane p-Methoxystyrene (40.8 g., 0.30 mole), 1,1-dichloro-2,2-difluoroethylene (55.8 g., 0.42 mole), and triethylamine (3.0 ml., 0.02 mole) are heated in a sealed tube (25 × 615 mm) at 125°–130°C. for 16 hrs. The cooled mixture is then poured into water, the reaction product extracted with ether, and the extracts washed with water, dried ($MgSO_4$), and evaporated to an oil. Distillation of the oil yields 69.0 g. (86%), b.p. 80°–85°C. (0.1 mm), of the desired intermediate suitable for use in the next step. Part of the oil was chromatographed (alumina, cyclohexane), and redistilled, b.p. 81°C. (0.02 mm), $n_D^{27}$ 1.5207.

Anal. C, 49.37; H, 3.86.

Procedure 2.
2-Chloro-1,1-difluoro-3-(p-methoxyphenyl)-2-cyclobutene

To a solution of 3.2 g. (0.049 mole) of 85% potassium hydroxide in 60 ml. of absolute ethanol there is added 10.7 g. (0.04 mole) of 2,2-dichloro-1,1-difluoro-3-(p-methoxyphenyl)cyclobutane. The mixture is heated at reflux for 1 hr. and then cooled to room temperature. Precipitated potassium chloride is removed by filtration and the filtrate concentrated to about 20 ml. About 70 ml. of water is added and the mixture is extracted with three 50 ml. portions of ether. The extract is washed (water 70 ml.), dried and the solvent distilled. The residual material constitutes a 96% yield of desired intermediate suitable for use in the next step. A small sample was distilled for analysis, b.p. 67°C. (0.02 mm) $n_D^{27}$ 1.5597.

Anal. C, 57.55; H, 3.90.

Procedure 3.
2-Chloro-3-p-methoxyphenyl)-2-cyclobuten-1-one.

2-Chloro-1,1-difluoro-3-(p-methoxyphenyl)-2-cyclobutene (215 g., 0.93 mole) is poured gradually into 272 ml. of concentrated $H_2SO_4$ with stirring. The rate of addition is adjusted to maintain the reaction temperature below 40°C. When the reaction subsides, the cooling bath is removed, but stirring is continued for 20 min. The mixture is poured into 3.1. of water. A precipitate forms, and is collected on a filter, washed with water, and air-dried. Recrystallization of this material twice from i-PrOH yields 128.8 g. (66%) of the desired intermediate, m.p. 96°–98°C. An analytical sample was prepared by chromatography on alumina (benzene) and recrystallized from heptane, m.p. 98°–100°C.

Anal. C, 63.24; H, 4.36; Cl, 16.87.

Procedure 4.
3-(p-Methoxyphenyl)cyclobutanone

2-Chloro-3-(p-methoxyphenyl)-2-cyclobuten-1-one (17.4 g., 0.084 mole), triethylamine (11.7 ml., 0.084 mole), and 2.1 g. of 10% Pd/C in 300 ml. of 10% aqueous methanol is shaken under $H_2$ (50 psi) until reduction is complete (30 min). The mixture is filtered and the filtrate evaporated. An ether solution of the residue is washed (water), dried ($MgSO_4$), and evaporated to give 15.4 g. of an oil which is chromatographed on alumina using benzene.

The second component eluted (4.8 g.) is distilled to give 4.3 g. of (29%) of the desired intermediate, b.p. 93°–95°C. (0.05 mm), $n_D^{27}$ 1.5449.

Anal. C, 75.03; H, 6.89.

Procedure 5.
1,3-bis(p-Methoxyphenyl)cyclobutanol p-Methoxyphenylmagnesium bromide is prepared in 30 ml. of tetrahydrofuran from Mg shavings (0.89 g., 0.037 gram atom) and 6.3 g. (0.034 mole) of p-bromoanisole. 3-(p-Methoxyphenyl)cyclobutanone (6.0 g., 0.034 mole) in 20 ml. of tetrahydrofuran is added dropwise at room temperature. The mixture is heated at reflux for 2 hrs., cooled and hydrolyzed with 5 ml. of saturated aqueous $NH_4Cl$. The solution is filtered and evaporated to give a residue which is dissolved in ether. The ether solution is washed (water), dried ($MgSO_4$), and evaporated to yield 9.9 g. of an oil. The latter is chromatographed on alumina. Impurities are first eluted with benzene, and the desired intermediate is eluted with chloroform (4.5 g.) and recrystallized from cyclohexane to yield 3.5 g. (36%), m.p. 71°–75°C.

Anal. C, 76.25; H, 6.91.

Procedure 6.
1,3-bis(p-Methoxyphenyl)cyclobutane 1,3-bis(p-methoxyphenyl)cyclobutanol (13.2 g., 0.046 mole), 3.0 g. of 10% Pd/C, 1 ml. of 70% $HClO_4$, and 100 ml. of 95% EtOH is shaken under 50 psi of $H_2$ until hydrogen absorption is complete. The catalyst is removed by filtration and the filtrate is evaporated. A solution of the residue in ether is washed (5% $NaHCO_3$, water) and dried ($MgSO_4$). Evaporation of the ether yields a residue (11.4 g.) which is recrystallized (EtOH), affording 6.8 g (55%) of the desired intermediate.

Anal. C, 80.46; H, 7.52.

Procedure 7.
1,3-bis-(p-Hydroxyphenyl)cyclobutane

A mixture of 1,3-bis-(p-methoxyphenyl)cyclobutane (13.57 g., 0.051 mole) and pyridine hydrochloride (46.8 g., 0.41 mole) is heated at 210°C. under a nitrogen atmosphere for 30 minutes and then poured into 500 ml. of water. Several ethyl acetate extracts are taken, combined, washed (dilute HCl, water), dried (MgSO$_4$), and evaporated. The desired product after recrystallization from benzene weighs 8.1 g. (67%), m.p. 148°–163.5°C.

Anal. C, 79.68; H, 6.93.

Nuclear magnetic resonance, dimethylsulfoxide-D$_6$, δ (ppm) (multiplicity, relative area): 2.37 (m,4); 3.37 (m, 2); 6.78 (m, 4); 7.18 (m, 4); 9.05 (s, 2).

Procedure 8.
3-(p-Methoxyphenyl)-1-[p-(2-tetrahydropyranyloxy)-phenyl]cyclobutanol The method of Procedure 5 is repeated with substitution of 8.9 g. (0.034 mole) of p-bromophenyl-2-tetrahydropyranyl ether for the p-bromoanisole specified in that example. The resulting product is obtained in 62% yield and is recrystallized from heptane, m.p. 72°–75°C.

Anal. C, 74.68; H, 7.42.

Nuclear magnetic resonance, CDCl$_3$ with tetramethylsilane as reference, δ (ppm)(multiplicity, relative area): 1.8 (m, 6); 2.18 (s, 1); 2.8 (m, 5); 3.73 (m, 2); 3.78 (s, 3); 5.45 (m, 1); 7.1 (m, 8).

Procedure 9.
1-(p-Hydroxyphenyl)-3-(p-methoxyphenyl)cyclobutane

A method of Procedure 6 is repeated substituting a product of Procedure 8 as starting material. The product is obtained in 67% yield and is recrystallized from aqueous ethanol, m.p. 96°–110°C.

Anal. C, 80.32; H, 7.08.

Nuclear magnetic resonance, CDCl$_3$ with tetramethylsilane as reference, δ (ppm)(multiplicity, relative area): 2.5 (m, 4); 3.5 (m, 2); 3.80 and 3.82 (s, 3); 4.96 (s, 1); 7.0 (m, 8).

The nmr spectral data for the products of Procedures 7 and 9 indicates that about a 60:40 ratio of geometric isomers was produced, but it was not determined whether the cis or the trans isomer was produced in larger amount.

Procedure 10.
1-(p-Benzyloxyphenyl)-3-(p-methoxyphenyl)-cyclobutanol and
1-(p-hydroxyphenyl)-3-(p-methoxyphenyl)cyclobutane The method of Procedure 5 is repeated with substitution of 8.9 g. (0.034 mole) of p-bromophenylbenzyl ether for the p-bromoanisole specified in that example. The resulting product is then hydrogenated under acidic conditions according to the method of Procedure 6 to yield the desired product.

Procedure 11.
3-(p-Methoxyphenyl)-1-(p-trityloxyphenyl)-cyclobutanol and
1-(p-hydroxyphenyl)-3-(p-methoxyphenyl)cyclobutane The method of Procedure 5 is repeated with substitution of 14.1 g. (0.034 mole) of p-bromophenyltrityl ether for the p-bromoanisole specified in that example. The resulting product is hydrogenated under acidic conditions according to the method of Procedure 6 to yield the desired product.

Procedure 12.
1[-p-(tert.-Butyloxy)phenyl]-3-(p-methoxyphenyl)-cyclobutanol and
1-(p-hydroxyphenyl)-3-(p-methoxyphenyl)cyclobutane The method of Procedure 5 is repeated with substitution of 7.8 g. of p-bromophenyl tert.-butyl ether for the p-bromoanisole specified in that example. The resulting product is hydrogenated under acidic conditions according to the method of Procedure 6 to yield the desired product.

What is claimed is:

1. A compound selected from the group consisting of 1,3-bis(p-hydroxyphenyl)cyclobutane and the monomethyl ether thereof.

2. The compound of claim 1, 1,3-bis(p-hydroxyphenyl)-cyclobutane.

3. The compound of Claim 1, 1-(p-hydroxyphenyl)-3-(p-methoxyphenyl)cyclobutane.

* * * * *